United States Patent
Chu

(10) Patent No.: US 8,236,013 B2
(45) Date of Patent: Aug. 7, 2012

(54) APPARATUS FOR PLACING MEDICAL IMPLANTS

(75) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1073 days.

(21) Appl. No.: 12/143,408

(22) Filed: Jun. 20, 2008

(65) Prior Publication Data

US 2009/0105743 A1 Apr. 23, 2009

Related U.S. Application Data

(60) Provisional application No. 60/981,159, filed on Oct. 19, 2007.

(51) Int. Cl.
*A61B 17/04* (2006.01)

(52) U.S. Cl. ........ 606/144; 606/139; 606/142; 606/145; 606/148

(58) Field of Classification Search .................. 606/139, 606/142, 144, 145, 148, 141
See application file for complete search history.

(56) References Cited

U.S. PATENT DOCUMENTS

| | | | |
|---|---|---|---|
| 5,364,408 A | 11/1994 | Gordon | |
| 5,391,174 A | 2/1995 | Weston | |
| 5,458,609 A | 10/1995 | Gordon et al. | |
| 5,470,338 A | 11/1995 | Whitfield et al. | |
| 5,474,568 A | 12/1995 | Scott | |
| 5,540,704 A | 7/1996 | Gordon et al. | |
| 5,578,044 A | 11/1996 | Gordon et al. | |
| 5,632,751 A | 5/1997 | Piraka | |
| 5,662,663 A | 9/1997 | Shallman | |
| 5,662,664 A | 9/1997 | Gordon et al. | |
| 5,713,910 A | 2/1998 | Gordon et al. | |
| 5,741,277 A | 4/1998 | Gordon et al. | |
| 5,860,992 A | 1/1999 | Daniel et al. | |
| 5,908,428 A | 6/1999 | Scirica et al. | |
| 5,964,782 A | 10/1999 | Lafontaine et al. | |
| 5,976,159 A | 11/1999 | Bolduc et al. | |
| 6,048,351 A | 4/2000 | Gordon et al. | |
| 6,051,006 A | 4/2000 | Shluzas et al. | |
| 6,071,289 A | 6/2000 | Stefanchik et al. | |
| 6,117,144 A | 9/2000 | Nobles et al. | |
| 6,245,079 B1 | 6/2001 | Nobles et al. | |
| 6,936,054 B2 | 8/2005 | Chu | |
| 6,955,643 B2 | 10/2005 | Gellman et al. | |
| 7,041,111 B2 | 5/2006 | Chu | |

(Continued)

OTHER PUBLICATIONS

International Preliminary Report on Patentability for PCT Application No. PCT/US2008/070032, mailed on Apr. 20, 2010, 8 pages.

(Continued)

*Primary Examiner* — Vy Q Bui

(57) ABSTRACT

An apparatus includes a carrier configured to be movably disposed within a channel defined by an elongate member. The carrier includes a proximal end portion and a distal end portion. The proximal end portion is configured to be coupled to an actuator. The distal end portion includes a protrusion and an engagement surface. The protrusion has a tip configured to bodily pierce tissue. The protrusion is configured to be received within a lumen defined by a connecting portion of an implant, such as, for example, a pelvic floor implant, such that the tip extends through the lumen defined by the connecting portion of the implant. The engagement surface is configured to engage a portion of the connecting portion of the implant to limit movement of the connecting portion of the implant relative to the protrusion.

24 Claims, 12 Drawing Sheets

U.S. PATENT DOCUMENTS

| | | |
|---|---|---|
| 7,048,749 B2 | 5/2006 | Kortenbach et al. |
| 7,122,039 B2 | 10/2006 | Chu |
| 2003/0191360 A1* | 10/2003 | Browning ................ 600/29 |
| 2004/0236356 A1 | 11/2004 | Rioux et al. |
| 2005/0107805 A1* | 5/2005 | Bouffier et al. ............ 606/119 |
| 2005/0222589 A1 | 10/2005 | Chu |
| 2005/0250977 A1 | 11/2005 | Montpetit et al. |
| 2006/0041263 A1 | 2/2006 | Chu et al. |
| 2006/0206119 A1 | 9/2006 | Chu |
| 2006/0229596 A1 | 10/2006 | Weiser et al. |
| 2007/0032695 A1 | 2/2007 | Weiser |
| 2007/0038017 A1 | 2/2007 | Chu |

OTHER PUBLICATIONS

International Search Report and Written Opinion for PCT/US2008/070032 mailed Mar. 19, 2009, 18 pages.

* cited by examiner

APPARATUS FOR PLACING MEDICAL IMPLANTS

CROSS-REFERENCE TO RELATED APPLICATIONS

This application claims priority to U.S. Provisional Patent Application Ser. No. 60/981,159, entitled "Apparatus for Placing Medical Implants," filed Oct. 19, 2007, which is incorporated herein by reference in its entirety.

BACKGROUND

The invention relates generally to medical devices and procedures, and more particularly to medical devices for placing sutures, implants and/or grafts within bodily tissue.

Known suturing devices can be used in surgical procedures to anchor grafts, anchor implants and/or approximate bodily tissue. For example, some known suturing devices can be used to apply sutures to approximate, ligate and/or fixate bodily tissue during an endoscopic procedure. For example, some known suturing devices can be used in minimally invasive procedures for repair of various pelvic dysfunctions, including hysteroceles, cystoceles, rectoceles and vaginal vault prolapse.

Some known suturing devices are used to place sutures that include a thin filament with a needle at the end for piercing bodily tissue. Because of the small size of the filament and the needle, such sutures can be difficult and/or hazardous to use in conjunction with known suturing devices. Moreover, some known suturing devices are not configured to place alternate suture designs, such as, for example, needle-less sutures, implant anchors and/or sutures configured to dilate bodily tissue.

Thus, a need exists for a suturing device for anchoring grafts and/or implants. Additionally a need exists for a suturing device that can be used with different types of sutures and/or implants.

SUMMARY

Medical devices for anchoring grafts and/or implants are described herein. In some embodiments, an apparatus includes a carrier configured to be movably disposed within a channel defined by an elongate member. The carrier includes a proximal end portion and a distal end portion. The proximal end portion is configured to be coupled to an actuator. The distal end portion includes a protrusion and an engagement surface. The protrusion has a tip configured to pierce bodily tissue. The protrusion is configured to be received within a lumen defined by a connecting portion of an implant, such as, for example, a pelvic floor implant, such that the tip extends through the lumen defined by the connecting portion of the implant. The engagement surface is configured to engage a portion of the connecting portion of the implant to limit movement of the connecting portion of the implant relative to the protrusion.

DETAILED DESCRIPTION

Figure 1:
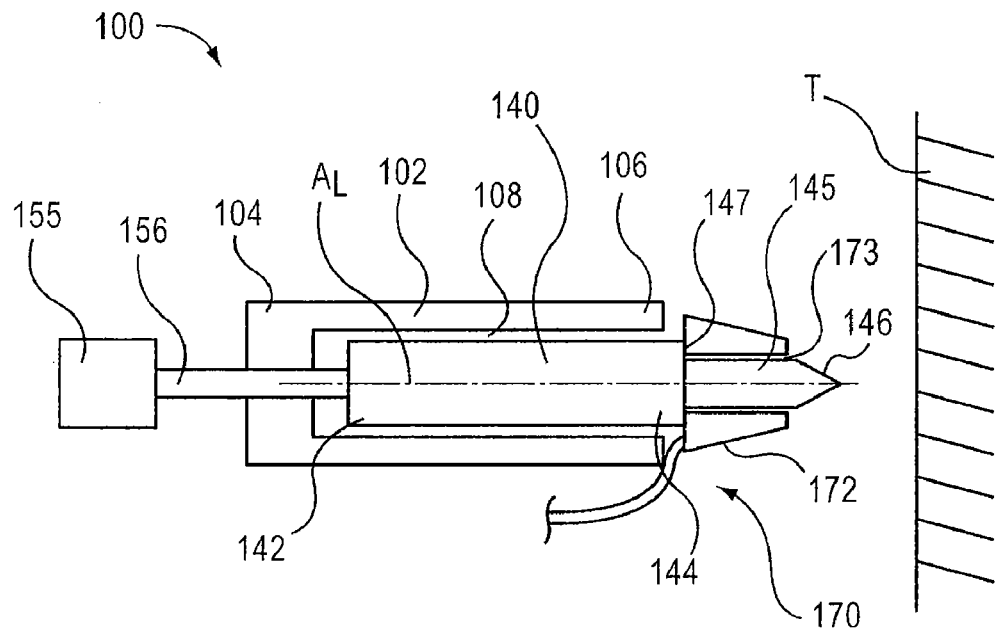
FIGS. 1 and 2 are schematic illustrations of a medical device according to an embodiment of the invention in a first configuration and a second configuration, respectively.

In some embodiments, an apparatus includes a carrier configured to be movably disposed within a channel defined by an elongate member. The carrier includes a proximal end portion and a distal end portion. The proximal end portion is configured to be coupled to an actuator. The distal end portion includes a protrusion and an engagement surface. The protrusion has a tip configured to pierce bodily tissue. The protrusion is configured to be received within a lumen defined by a connecting portion of an implant, such as, for example, a pelvic floor implant, such that the tip extends through the lumen defined by the connecting portion of the implant. The engagement surface is configured to engage a portion of the connecting portion of the implant to limit movement of the connecting portion of the implant relative to the protrusion. For example, in some embodiments, the engagement surface is configured to limit movement of the connecting portion of the implant proximally relative to the protrusion while allowing movement of the connecting portion of the implant distally relative to the protrusion.

In some embodiments, an apparatus includes an elongate member, an actuator and a carrier. The elongate member has a proximal end portion and a distal end portion. The actuator is coupled to the proximal end portion of the elongate member. The carrier is movably coupled to the distal end portion of the elongate member. In some embodiments, for example, the distal end portion of the elongate member can define a channel within which the distal end portion of the carrier is movably disposed. The carrier includes a proximal end portion and a distal end portion. The proximal end portion is configured to be coupled to the actuator, which can be, for example, mechanical rod. The distal end portion is configured to be received by and disposed within a lumen defined by a connecting portion of an implant. The distal end portion of the carrier includes an engagement surface configured to engage the connecting portion of the implant to limit movement of the connecting portion of the implant relative to the distal end portion of the carrier.

In some embodiments, an apparatus includes an elongate member and a carrier. The elongate member has a distal end portion. The carrier is movably coupled to the elongate member for movement between a first position and a second position. In the second position, the distal end portion of the carrier is extended from the distal end portion of the elongate member. The distal end portion of the carrier is configured to be received within lumen defined by a connecting portion of an implant. The distal end portion of the carrier includes an engagement surface configured to engage the connecting portion of the implant to retain the distal end portion of the carrier within the lumen defined by the connecting portion of the implant when the carrier is moved between the first position and the second position.

In some embodiments, an apparatus includes an implant configured to support an anatomical structure, such as, for example, a pelvic floor implant. The implant has a connector configured to removably engage a carrier of an implant delivery device such that the connector is moved distally with the carrier when the carrier is moved distally. The connector includes an inner surface and a retention surface. The inner surface defines a lumen configured to receive the carrier of the implant delivery device. The retention surface is configured to engage a retaining portion of the delivery device such that movement of the connector is limited when the carrier is moved proximally.

In some embodiments, a kit includes an implant delivery device and an implant. The implant delivery device has a carrier movably coupled to a distal end portion of the implant delivery device. The carrier includes a proximal end portion configured to be coupled to an actuator, and a distal end portion including an engagement surface. The implant is configured to support an anatomical structure and has a connecting portion defining a lumen configured to receive the carrier of the implant delivery device. The engagement surface of the carrier is configured to engage the connecting portion of the implant to limit movement of the connecting portion of the implant relative to the distal end portion of the carrier.

As used in this specification and the appended claims, the words "proximal" and "distal" refer to the direction closer to and away from, respectively, an operator (e.g., surgeon, physician, nurse, technician, etc.) who would insert a medical device into the patient, with the tip-end (i.e., distal end) of the device inserted inside a patient's body first. Thus, for example, the end of a medical device first inserted inside a patient's body is the distal end, while the end of the medical device to last enter the patient's body or the end of the medical device extending from the patient's body during a procedure is the proximal end. Moreover, the movement of the distal end of a medical device within the body can, in certain situations, be considered as movement in the distal direction even though the distal end of the medical device may be moving towards the operator of the medical device. For example, the movement of the distal end of a medical device along a curved path within the patient's body can be considered as distal movement.

Figure 2:
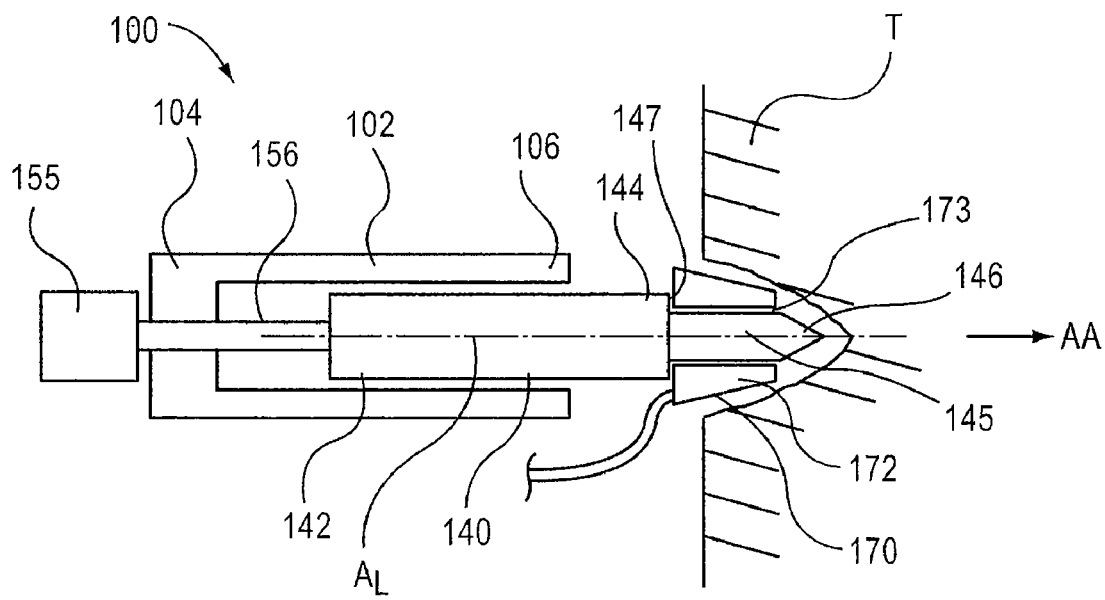

FIGS. 1 and 2 are schematic illustrations of a suturing device 100 and a portion of an implant 170 according to an embodiment of the invention in a first configuration and a second configuration, respectively. The suturing device 100 includes an elongate member 102, a carrier 140 and an actuator 155. The elongate member 102 has a proximal end portion 104 and a distal end portion 106 and defines a channel 108 therein. The carrier 140 is disposed within the channel 108 such that the carrier 140 can move along a longitudinal axis $A_L$ of the channel 108 between a first position (FIG. 1) and a second position (FIG. 2), as indicated by the arrow AA in FIG. 2. The longitudinal axis $A_L$ can, for example, pass lengthwise (e.g., from the proximal end portion 104 to the distal end portion 106) through the centroid of the elongate member 102 and/or the channel 108 (e.g., the longitudinal axis $A_L$ can be a centroidal axis of the elongate member 102 and/or the channel 108). When the carrier 140 is in the first position, the suturing device 100 is said to be in its first configuration. Similarly, when the carrier 140 is in the second position, the suturing device 100 is said to be in its second configuration.

The carrier 140 has a proximal end portion 142 and a distal end portion 144. The proximal end portion 142 of the carrier 140 is coupled to the actuator 155 by a coupler 156. The distal end portion 144 of the carrier 140 includes a protrusion 145 and an engagement surface 147. The protrusion 145 has a tip 146 configured to pierce bodily tissue T, which can be, for example, pelvic tissue (e.g., a sacrospinous ligament, a tendineus arch of levator muscle and/or an iliococcygeus muscle). As shown, the protrusion 145 can be received by and disposed within a lumen 173 defined by a connecting portion 172 of the implant 170 such that the distal portion of the tip 146 extends through the lumen 173. Said another way, the protrusion 145 can be received within the lumen 173 such that the distal portion of the tip 146 is disposed outside of the lumen 173 defined by the connecting portion 172 of the implant 170. Moreover, the protrusion 145 can be received within the lumen 173 such that the engagement surface 147 of the carrier 140 contacts and/or engages a portion of the connecting portion 172 of the implant 170.

In this manner, the engagement surface 147 of the carrier 140 can limit movement of the connecting portion 172 of the implant 170 relative to the carrier 140. For example, in some embodiments, the engagement surface 147 of the carrier 140 can limit movement of the connecting portion 172 of the implant 170 proximally relative to the carrier 140 while allowing movement of the connecting portion 172 of the implant 170 distally relative to the carrier 140. In other embodiments, the engagement surface 147 of the carrier 140 can limit movement of the connecting portion 172 of the implant 170 both proximally and distally relative to the carrier 140.

The suturing device 100 can be used to place at least a portion of the implant 170 within the bodily tissue T, as described below. The implant 170 can be loaded onto the suturing device 100 when the suturing device 100 is in the first configuration (i.e., when the carrier 140 is in its first, or retracted, position, as shown in FIG. 1). To load the implant 170, the connecting portion 172 of the implant is disposed at the distal end portion 106 of the elongate member 102 such that the protrusion 145 of the carrier 140 is received within the lumen 173 defined by the connecting portion 172. Although the tip 146 is shown as being disposed distally outside of the lumen 173 when the suturing device 100 is in the first configuration, in other embodiments, the carrier 140 can be disposed within the channel 108 of the elongate member 102 such that the tip 146 is disposed within the lumen 173 (i.e., the tip 146 does not extend outside of the lumen 173) when the suturing device 100 is in the first configuration. In yet other embodiments, the carrier 140 can be disposed within the channel 108 of the elongate member 102 such that the tip 146 is disposed entirely within the in channel 108 (i.e., the tip 146 is not disposed within the lumen 173) when the suturing device 100 is in the first configuration. Said another way, in some embodiments, the connecting portion 172 can contact and/or engage the distal end portion 106 of the elongate member 102 when the suturing device 100 is in the first configuration.

Similarly, although the engagement surface 147 of the carrier 140 is shown as being in contact with the connecting portion 172 of the implant 170 when the suturing device 100 is in the first configuration, in other embodiments, the engagement surface 147 can be spaced apart from the connecting portion 172 of the implant 170 when the suturing device 100 is in the first configuration. For example, in some embodiments, the connecting portion 172 of the implant can be in contact with distal end portion 106 of the elongate member 102 when the suturing device 100 is in the first configuration.

The suturing device 100 can be disposed within the body until the connecting portion 172 of the implant 170 and/or the distal end portion 106 of the elongate member 102 is in contact with and/or adjacent to the bodily tissue T. The suturing device 100 can be disposed within the body by any suitable means, such as, for example, via an endoscope. When the suturing device 100 is suitably disposed within the body, the actuator 155 can be used to move the carrier 140 within the channel 108 of the elongate member 102 from its first position (FIG. 1) to its second position (FIG. 2), as indicated by the arrow AA in FIG. 2. In this manner, the suturing device 100 can be moved from its first configuration to its second configuration. The actuator 155 can be any suitable actuator, such as, for example, a mechanical actuator, an electronic actuator, a hydraulic actuator, a pneumatic actuator or the like. Similarly, the coupler 156 can be any suitable member for operatively coupling the actuator 155 to the proximal end portion 104 of the carrier 140. In some embodiments, for example, the coupler 156 can be a mechanical linkage.

When the carrier 140 moves from its first position (FIG. 1) to its second position (FIG. 2), the tip 146 of the carrier 140 pierces the bodily tissue T, thereby defining a passageway within the tissue T for receiving at least a portion of the implant 170. Moreover, when the carrier 140 is moved from its first position to its second position, the engagement surface 147 of the carrier 140 contacts a portion of the connecting portion 172 of the implant 170, such that the connecting portion 172 moves distally with the carrier 140 and into the passageway defined within the bodily tissue T. Said another way, when the carrier 140 is moved from its first position to its second position, the engagement surface 147 of the carrier 140 contacts a portion of the connecting portion 172 of the implant 170 such that movement of the connecting portion 172 of the implant 170 proximally relative to the carrier 140 is limited. In this manner, the passageway within the tissue T can be defined and the implant 170 can be disposed within the passageway in one operation.

When the connecting portion 172 is secured within the bodily tissue T, the actuator 155 can be used to move the carrier 140 within the channel 108 of the elongate member 102 from its second position back to its first position. Accordingly, the distal end 144 of the carrier 140 is moved distally relative to the connecting portion 172 of the implant 170, thereby leaving the implant 170 disposed within the tissue T. The suturing device 100 can then be removed from the body.

Figure 3:
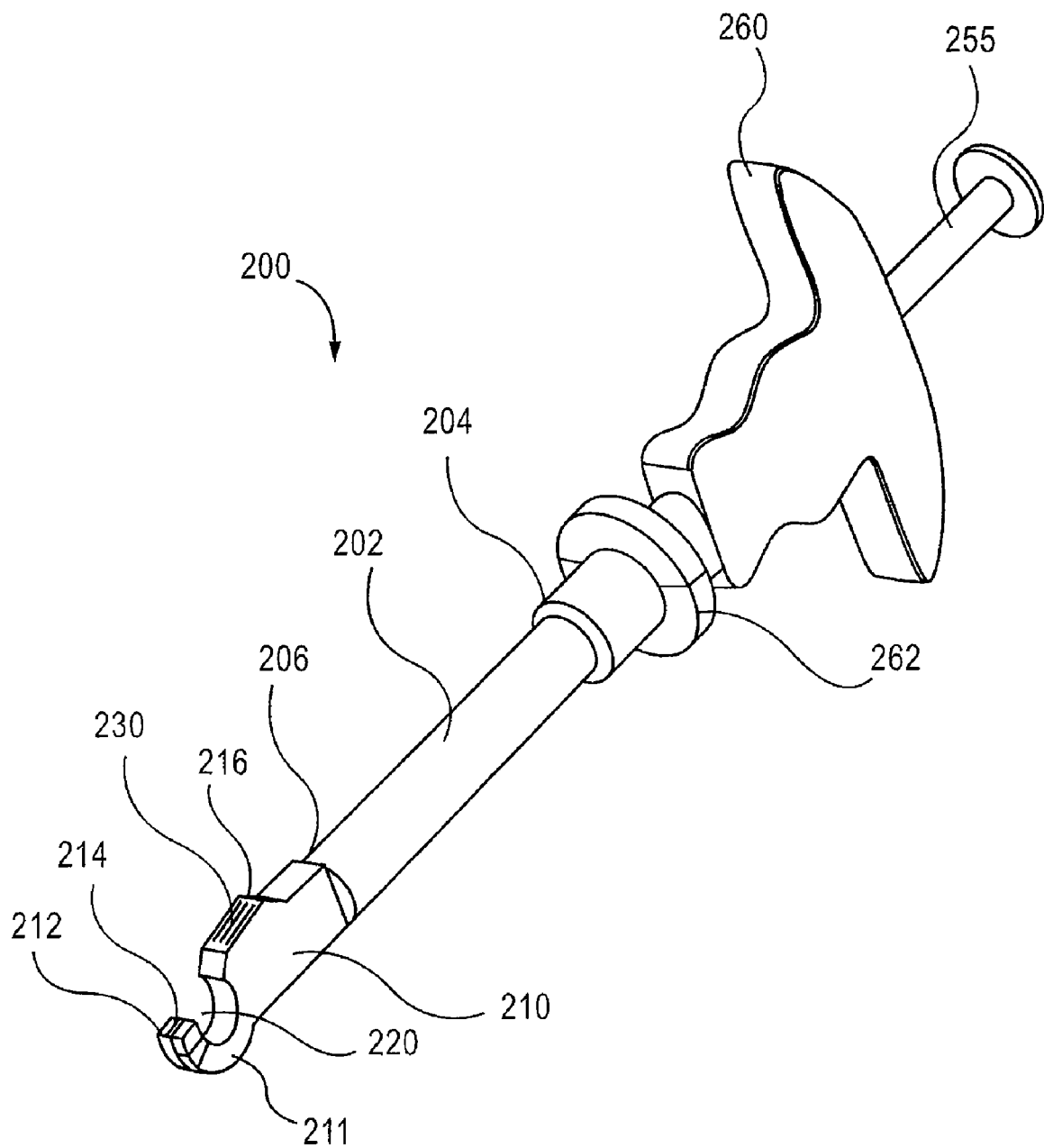
FIG. 3 is a perspective view of a medical device according to an embodiment of the invention in a first configuration.
Figure 4:
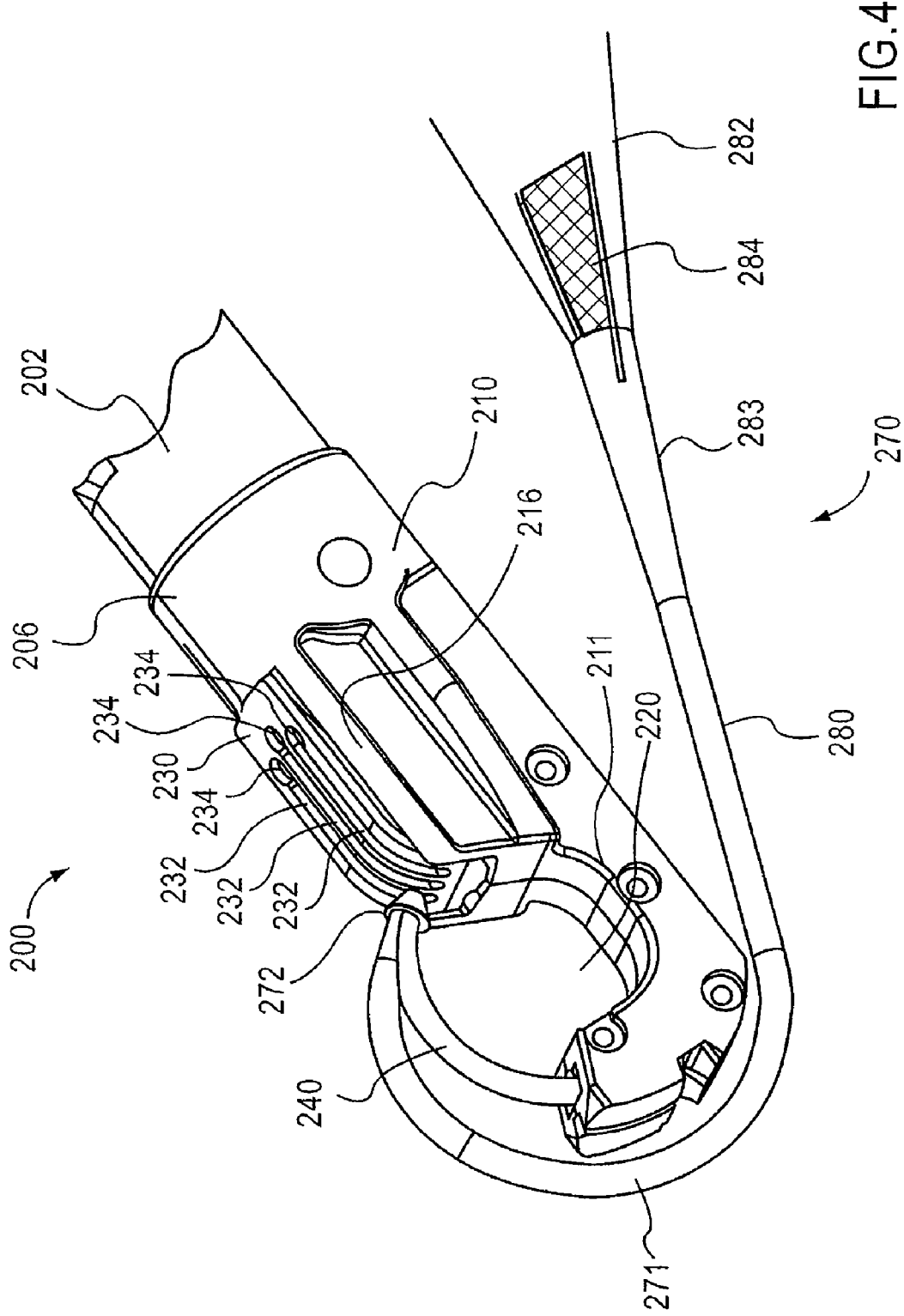
FIG. 4 is a perspective view of a portion of the medical device shown in FIG. 3 in a second configuration coupled to an implant according to an embodiment of the invention.
Figure 5:
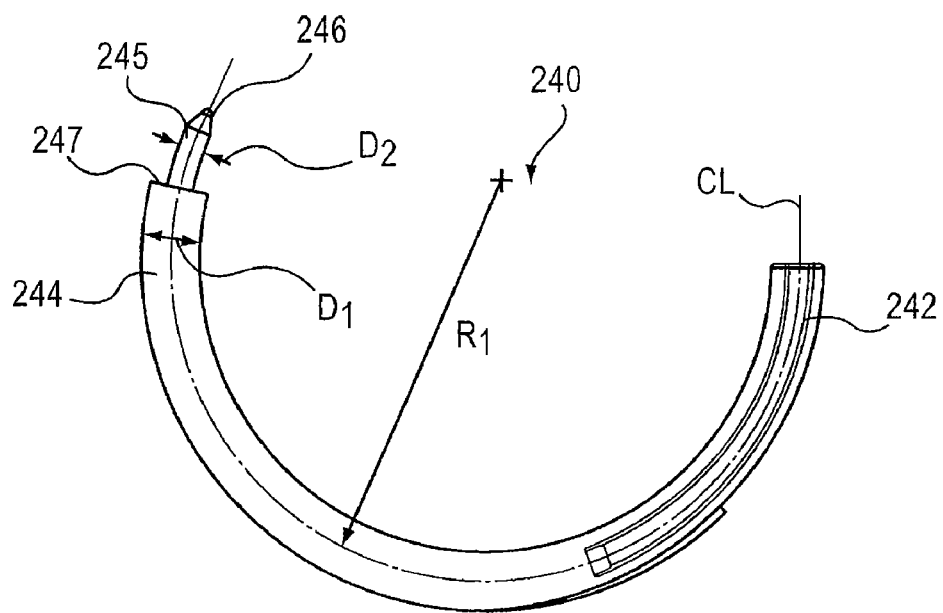
FIG. 5 is a side view of a portion of the medical device shown in FIG. 3.
Figure 6:
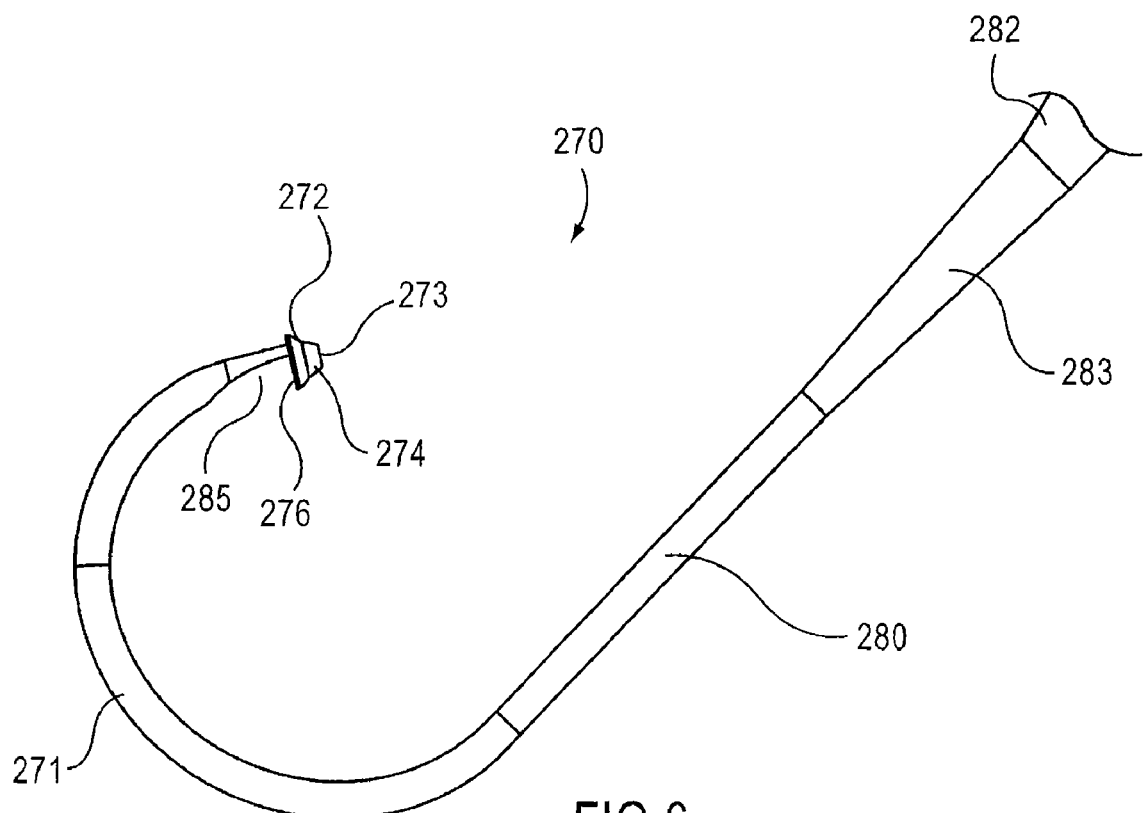
FIG. 6 is a side view of the implant shown in FIG. 4.

FIGS. 3-10 illustrate a suturing device 200 and an implant 270 according to an embodiment of the invention. Although FIGS. 3-10 show the same embodiment, certain reference numerals and/or features are omitted in some of the figures for clarity. FIG. 3 is a perspective view of the suturing device 200 in a first (i.e., retracted) configuration. FIG. 4 is a perspective view of the distal portion of the suturing device 200 in a second (i.e., extended) configuration coupled to a distal portion 271 of an implant 270. FIG. 5 is a side view of the carrier 240 of the suturing device 200. FIG. 6 is a side view of the implant 270. FIGS. 7-10 are cross-sectional side views of the suturing device and the implant 270 in the first configuration (i.e., a retracted configuration with the implant 270 loaded), a third configuration (i.e., a partially extended configuration), the second configuration (i.e., the extended configuration) and a fourth configuration (i.e., a retracted configuration after placement of the implant 270), respectively.

The suturing device 200 includes an elongate member 202, a carrier 240 (see e.g., FIG. 5), a handle 260 and actuator 255. The elongate member 202 has a proximal end portion 204 and a distal end portion 206 and defines a channel 208 (see FIGS. 7-10). As described in more detail herein, the carrier 240 is movably disposed within a curved portion 224 of the channel 208.

As shown in FIG. 3, the handle 260 is coupled to the proximal end portion 204 of the elongate member 202. A retaining ring 262 is movably disposed about the proximal end portion 204 of the elongate member 202 adjacent the handle 260. The retaining ring 262 can include openings, slots and/or any other suitable mechanism for releasably retaining a portion of the implant 270 when the suturing device 200 is in use. Examples of a suitable retaining ring 262 are shown and described in U.S. patent application Ser. No. 11/435,708 entitled "Tying Knots," filed May 16, 2006, which is incorporated herein by reference in its entirety.

The actuator 255 is slidably disposed within the handle 260 such that a portion of the actuator 255 is disposed within the channel 208 and is in contact with a flexible coupling rod 256 (see e.g., FIGS. 7-10). The coupling rod 256 is in contact with a proximal end portion 242 of the carrier 240. Accordingly, as discussed in more detail herein, the actuator 255 can be used to move the carrier 240 within the curved portion 224 of the channel 208. In some embodiments, the suturing device 200 can include a biasing member (not shown in FIGS. 3-10) configured to bias the actuator 255, the coupling rod 256 and/or the carrier 240 in a predetermined position within the channel 208. For example, in some embodiments a spring can be disposed between the actuator and a portion of the handle (e.g., the spring can be located either inside of the handle 260 or outside of the handle 260) to urge the actuator in its proximal position (i.e., the position as shown in FIG. 3). In this manner, the suturing device 200 can be maintained and/or biased in its first (i.e., retracted) configuration.

The distal end portion 206 of the elongate member 202 includes a delivery head 210 having a first surface 212, a second surface 216 and a curved portion 211 between the first surface 212 and the second surface 216. The first surface 212 is spaced apart from the second surface 216 such that an opening 220 is defined between the first surface 212 and the second surface 216, bounded by the curved portion 211. The first surface 212 defines an opening 214 in communication with the curved portion 224 of the channel 208 (see e.g. FIG. 10). The second surface 216 defines an opening 218 about which a retainer 230 is disposed. As shown in FIG. 4, the retainer 230, which is also referred to as a "catch," defines three openings 232 each having an enlarged portion 234. The portions of the retainer 230 defining the three openings 232 can be referred to as "ribs."

The carrier 240 is a tubular member (i.e., the carrier 240 has a circular cross-sectional area) and has a proximal end portion 242 and a distal end portion 244, and defines a center line CL.

The carrier 240 is curved such that the center line CL defines a radius of curvature $R_1$. As shown in FIGS. 7-10, the proximal end portion 242 of the carrier 240 is in contact with and/or coupled to the connecting rod 256. In this manner, the carrier 240 is operatively coupled to the actuator 255 such that when the actuator 255 moves relative to the handle 260, the carrier 240 moves within the curved portion 224 of the channel 208.

The distal end portion 244 of the carrier 240 includes a protrusion 245 and an engagement surface 247. The protrusion 245 is substantially solid (i.e., is devoid of openings therein) and has a tip 246 configured to pierce bodily tissue T (see e.g., FIGS. 7-10). The bodily tissue T can be, for example, pelvic tissue (e.g., a sacrospinous ligament, a tendineus arch of levator muscle and/or an iliococcygeus muscle). The engagement surface 247 is substantially normal to the center line CL of the carrier 240. Said another way, the center line CL of the carrier 240 and a line defined to include a portion of the engagement surface 247 intersect at an angle of approximately 90 degrees. For example, when the engagement surface 247 is planar, a plane defined by the engagement surface 247 intersects the center line CL of the carrier at an angle of approximately 90 degrees.

As shown in FIG. 5, the diameter $D_2$ of the protrusion 245 is less than the diameter $D_1$ of the remaining portions of the carrier 240. The size of the engagement surface 247 is associated with the difference in the diameter $D_1$ of the carrier 240 and the diameter $D_2$ of the protrusion 245. Said another way, the engagement surface 247 is the shoulder or step between the diameter $D_1$ of the carrier 240 and the diameter $D_2$ of the protrusion 245. In some embodiments, the diameter $D_2$ of the protrusion 245 is approximately three quarters the diameter $D_1$ of the carrier 240. In other embodiments, the diameter $D_2$ of the protrusion 245 is approximately half the diameter $D_1$ of the carrier 240. In yet other embodiments, the diameter $D_2$ of the protrusion 245 is approximately one quarter the diameter $D_1$ of the carrier 240. In some embodiments, for example, the diameter $D_1$ of the carrier can be between 10 and 12 mm. In other embodiments, the diameter $D_1$ of the carrier can be between 12 and 15 mm.

As shown in FIGS. 4 and 6, the implant 270 includes a distal portion 271, a dilator 280, a sleeve 282 and a strap 284. The distal portion 271 of the implant 270 includes a connector 272 and defines an opening 285. The connector 272 includes an outer surface 274, an inner surface 275 and a retention surface 276. The inner surface 275 defines a lumen 273 therethrough. As described in more detail herein, the protrusion 245 of the carrier 240 can be disposed through the opening 285 and within the lumen 273 defined by the inner surface 275 of the connector 272 such that the tip 246 extends through the lumen 273 (see e.g. FIGS. 8 and 9).

Moreover, the protrusion 245 can be received within the lumen 273 such that the engagement surface 247 of the carrier 240 contacts and/or engages a portion of the retention surface 276 of the connector 272. In this manner, the engagement surface 247 of the carrier 240 can selectively limit movement of the connector 272 of the implant 270 relative to the carrier 240. Said another way, when the carrier 240 moves as indicated by the arrow CC in FIG. 8, the engagement surface 247 of the carrier 240 contacts and/or engages the retention surface 276 of the connector 272 such that the connector 272 moves with the carrier 240. When the carrier 240 moves as indicated by the arrow EE in FIG. 10, the engagement surface 247 of the carrier 240 becomes disengaged from the retention surface 276 of the connector 272 such that the carrier 240 moves relative to the connector 272.

Figure 7:
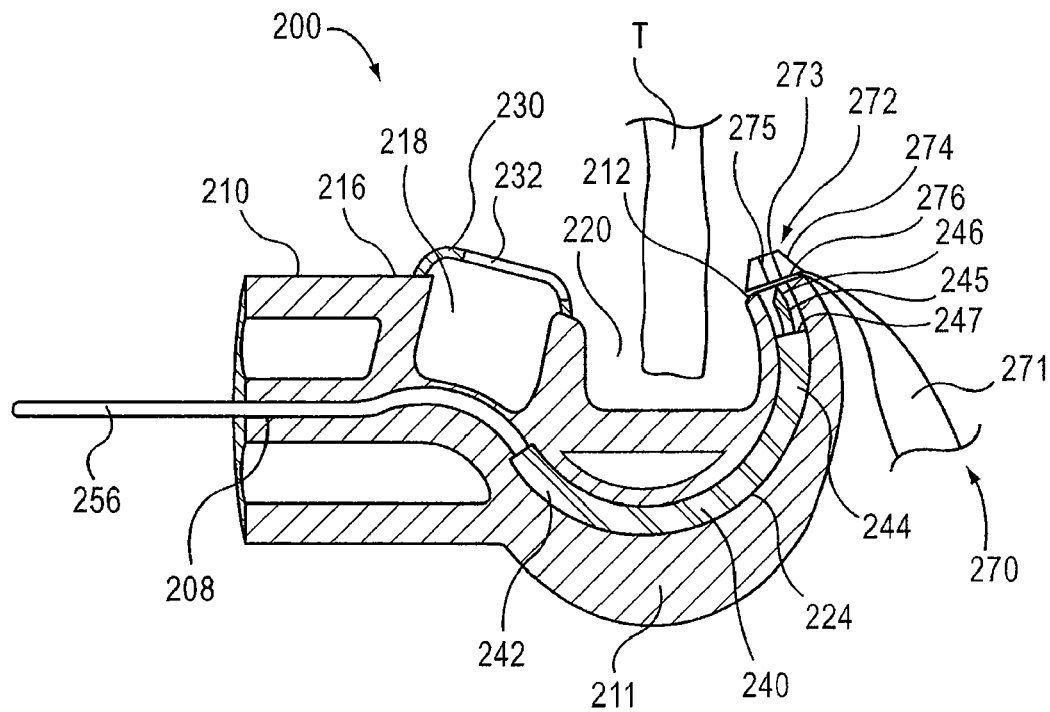
FIGS. 7-10 are cross-sectional side views of the portion of the medical device and the implant shown in FIG. 4 in a first configuration, a third configuration, the second configuration and a fourth configuration, respectively.

The suturing device 200 can be used to place the implant 270 within the bodily tissue T, as described below with reference to FIGS. 7-10. As shown in FIG. 7, the connector 272 of implant 270 can be placed or "loaded" onto the suturing device 200 when the suturing device 200 is in the first configuration. When the suturing device 200 is in the first configuration, the tip 246 of the protrusion is disposed within the curved portion 224 of the channel 208. Accordingly, to load the implant 270, the connecting portion 272 of the implant is disposed against the delivery head 210 such that at least a portion of the retention surface 276 of the connector 272 contacts at least a portion of the first surface 212 of the delivery head 210.

In some embodiments, the connector 272 can be removably coupled to the first surface 212 of the delivery head 210. In this manner, the implant 270 can remain loaded onto the suturing device 200 prior to use (e.g., when the suturing device is placed on a surgical tray or the like). In some embodiments, for example, the connector 272 can include a retaining mechanism, such as a tab or protrusion (not shown in FIGS. 7-10) that is received within a mating recess or opening defined by the first surface 212 to removably couple the connector 272 to the delivery head 210. In other embodiments, a portion of the distal portion 271 of the implant can be received within an opening or notch defined by the delivery head to removably couple the implant 270 to the delivery head.

The suturing device 200 and the implant 270 can be disposed within the body such that a portion of the bodily tissue T is within the opening 220 defined between the first surface 212 and the second surface 216 of the delivery head 210. The suturing device 200 can be disposed within the body by any suitable means, such as, for example, via an endoscope. When the suturing device 200 is suitably disposed within the body, the actuator 255 can be moved distally relative to the handle 260, thereby causing the flexible coupling rod 256 to move within the channel 208 as indicated by the arrow BB in FIG. 8. The translation of the coupling rod 256 within the channel 208 causes the carrier 240 to move within the curved portion 224 of the channel 208 as indicated by the arrow CC in FIG. 8. In this manner, the suturing device 200 can be moved from the retracted configuration to the partially extended configuration.

Figure 8:
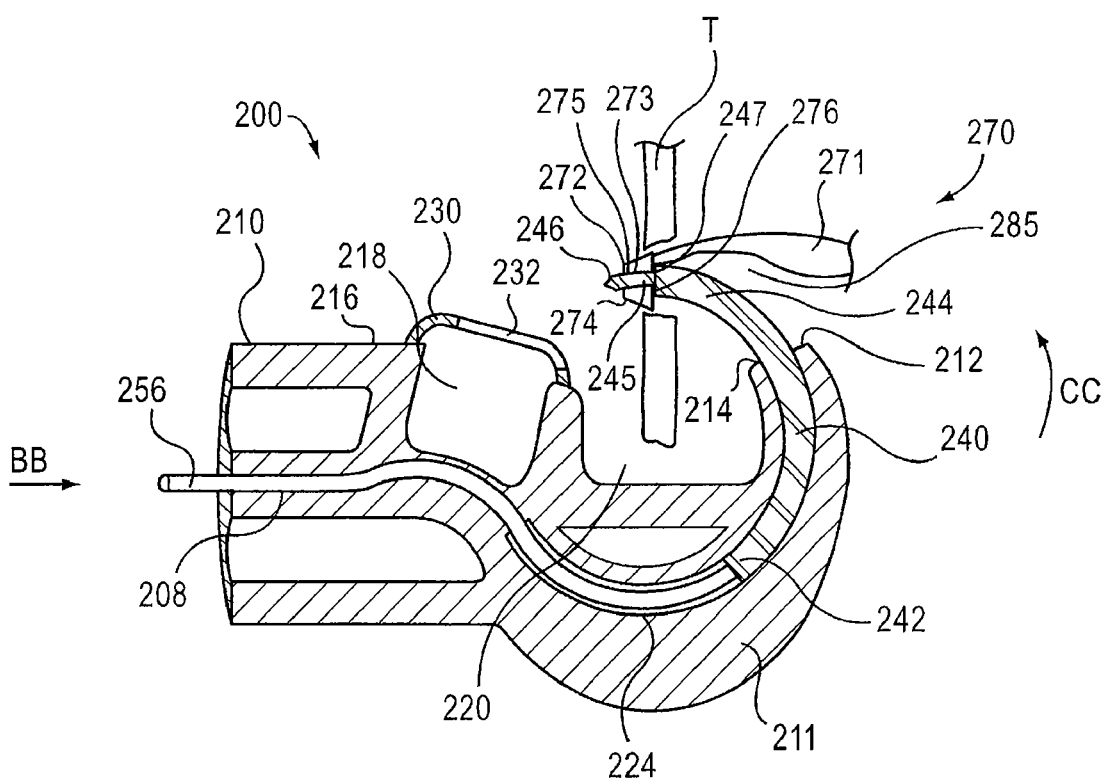

When the suturing device 200 is in the partially extended configuration, as shown in FIG. 8, the distal end portion 244 of the carrier 240 is disposed through the opening 214 defined by the first surface 212 of the delivery head 210 and outside of the curved portion 224 of the channel 208. The distal end portion 244 of the carrier 240 is further disposed within the opening 285 defined by the distal portion 271 of the implant such that the protrusion 245 is received within the lumen 273 defined by the inner surface 275 of the connector 272. As shown, when the suturing device 200 is in the partially extended and extended configurations, the tip 246 extends through the lumen 273 (i.e., the distal portion of the tip 246 is disposed outside of the lumen 273). Moreover, the engagement surface 247 of the carrier 240 contacts the retention surface 276 of the connector 272 such that the connector 272 moves with the carrier 240 when the carrier 240 moves in the direction as indicated by the arrow CC in FIG. 8.

As shown in FIG. 8, when the carrier 240 moves in the direction as indicated by the arrow CC, the tip 246 of the protrusion can pierce the tissue T to define a passageway within the tissue T through which a portion of the implant 270 (e.g., the distal portion 271, the dilator 280 and/or the strap 284) can be placed. The continued movement of the carrier 240 causes the connector 272 to be inserted through and/or enlarge the passageway through the tissue T. As shown, the outer surface 274 of the connector 272 is tapered to help the connector further define and/or enlarge the passageway through the tissue.

Figure 9:
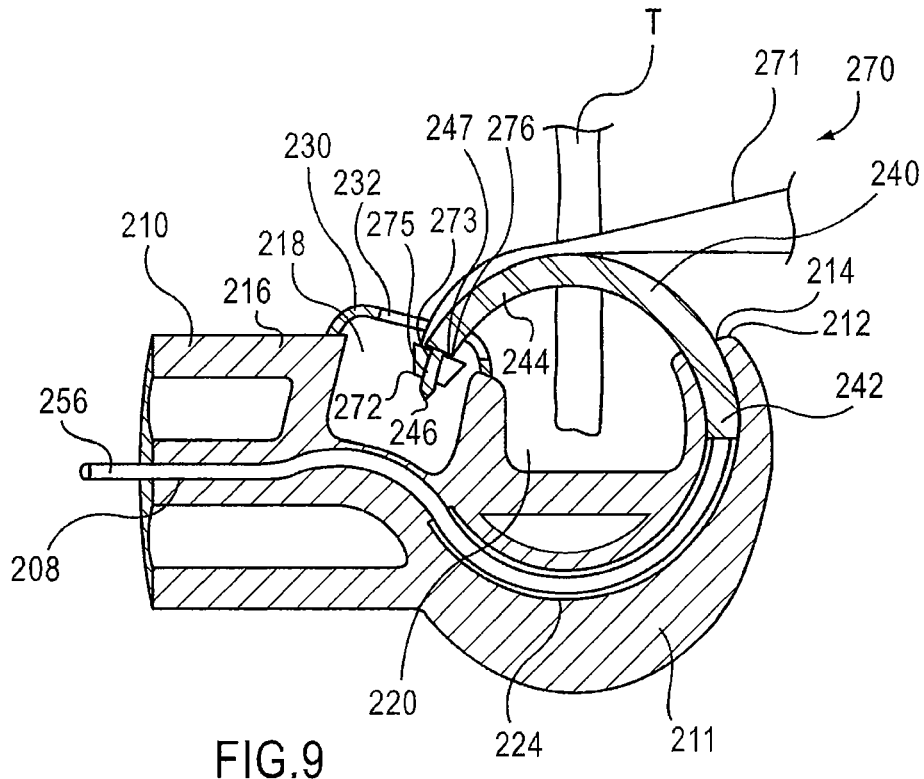

Continued movement of the actuator 255 causes carrier 240 to move until the tip 246 of the carrier 240 and/or the connector 272 of the implant 270 contacts the retainer 230. The openings 232 defined by the retainer 230 are smaller than the widest portion of the connector 272 thereby defining an interference fit between the connector 272 and the retainer 230. For example, in the illustrated embodiment, the widest portion of the connector 272 is the diameter of the retention surface 276. Thus, diameter of the retention surface 276 forms an interference fit with the retainer 230 when disposed within the openings 232 defined by the retainer. Accordingly, continued movement of the actuator 255 causes the portions of the retainer 230 (e.g., the "ribs") defining the openings 232 to deflect thereby allowing the connector 272 to be disposed through one of the openings 232. In this manner, the suturing device 200 can be placed into the extended configuration, as shown in FIG. 9.

When the suturing device 200 is in the extended configuration, the distal end portion 244 of the carrier 240 and the connector 272 of the implant 270 are disposed through one of the openings 232 defined by the retainer 230 and into the opening 218 defined by the second surface 216 of the delivery head 210. Said another way, the connector 272 is disposed within the "catch" (i.e., the retainer 230). Moreover, the distal end portion 271 of the implant 270 is disposed within the passageway through the tissue T. After the suturing device 200 has been placed in the extended configuration, the actuator 255 can be moved proximally relative to the handle 260, thereby causing the coupling rod 256 to move within the channel 208 as indicated by the arrow DD in FIG. 10. The translation of the coupling rod 256 within the channel 208 causes the carrier 240 to move within the curved portion 224 of the channel 208 as indicated by the arrow EE in FIG. 10. In this manner, the suturing device 200 can be moved from the extended configuration back to the retracted configuration. In some embodiments, for example, the suturing device 200 can be moved from the extended configuration back to the retracted configuration by a biasing member (not shown in FIGS. 3-10).

Because the retainer 230 defines an interference fit between the connector 272 and the retainer 230 when the carrier 240 moves from the extended configuration to the retracted configuration, the connector 272 is retained within the opening 218. Said another way, the distal end 244 of the carrier 240 is moved relative to the connector 272 of the implant 270, thereby leaving the connector 272 within the opening 218. Said yet another way, when the carrier 240 moves from the extended configuration (FIG. 9) to the retracted configuration (FIG. 10), the engagement surface 247 of the carrier 240 is spaced apart from the retention surface 276 of the connector 272 such that the connector 272 does not move with the carrier 240 when the carrier 240 moves in the direction as indicated by the arrow EE in FIG. 10. Accordingly, the carrier 240 moves in the direction as indicated by the arrow EE back through the passageway defined through the tissue T such that only the distal end portion 271 of the implant 270 is within the tissue.

The suturing device 200 can then be moved within the body such that the bodily tissue T is no longer within the opening 220. Because the connector 272 is retained within the opening 218, movement of the suturing device 200 causes the implant 270 to move within the tissue T. In this manner, the implant 270 can be positioned and/or tensioned within the tissue T, as desired. When the implant 270 is suitably positioned within the tissue T, the connector 272 can be removed from the retainer 230 via the enlarged portion 234 of the opening 232.

The strap 284, which can also be referred to as an arm, a support member and/or an implant member, is configured to engage bodily tissue T to retain the implant 270 in its desired position and/or support an anatomical structure when disposed within the body. In some embodiments, for example, the strap 284 can be constructed from a mesh material configured to promote tissue in-growth to enhance the anchoring of the implant 270. Similarly, in some embodiments, the strap 284 can include roughened and/or jagged edges to enhance the anchoring of the implant 270 within the tissue T. In some embodiments, for example, the strap 284 can include protrusions or "tangs" along an edge of the strap 284 to enhance the anchoring of the implant 270 within the tissue T.

The sleeve 282 is coupled to an end of the dilator 280 and houses or encloses the strap 284. The sleeve 282 is constructed from a smooth material and provides for a smooth transition of the strap 284 through the tissue T during insertion of the implant assembly 270. For example, in some embodiments, the sleeve 282 can help prevent the strap 284 from prematurely engaging the tissue T during delivery. Similarly, the dilator 280 is constructed from a smooth material and has a tapered portion 283. In this manner, when the implant 270 is being placed within the tissue T, the dilator can enlarge the passageway within the tissue T so that the sleeve 282 and the strap 284 can be positioned within the tissue as desired.

Figure 10:
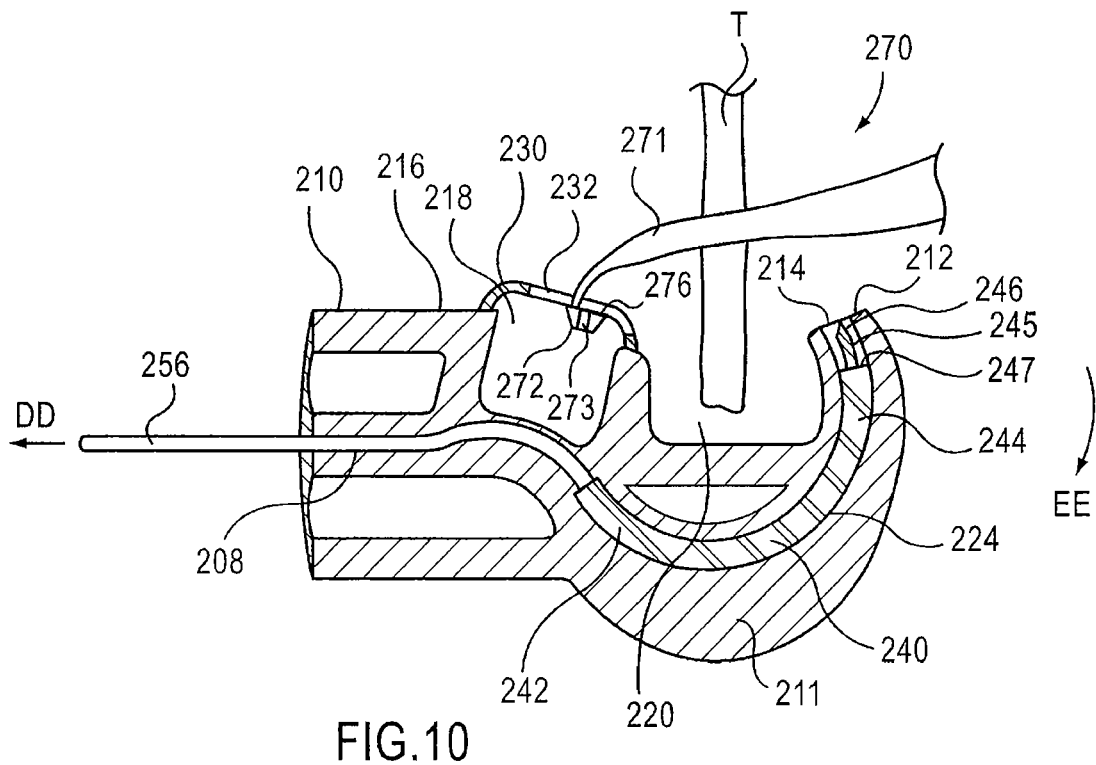

When the implant 270 is properly positioned and tensioned within the tissue T as described above, the sleeve 282 and/or the dilator 280 can be removed from the strap 284 (not shown in FIG. 10). In this manner, the strap 284 can engage the surrounding tissue T to secure the implant 270 in position.

The components of the suturing device 200 can be constructed from any suitable biocompatible material. For example, in some embodiments, the elongate member 202, the delivery head 210, the actuator 255 and/or the handle 260 can be constructed from any suitable medical grade plastic, such as polypropylene, polycarbonate or glass-filled polycarbonate. In some embodiments, the carrier 240 can be constructed a metal alloy, such as stainless steel. In some embodiments, the coupling rod 256 can be constructed from a flexible material, such as stainless steel, Nitinol or the like.

Similarly, the components of the suturing device 200 can be constructed using any suitable manufacturing process or combination of manufacturing processes. For example, in some embodiments, the elongate member 202 can be constructed from a medical grade plastic using an extrusion process. In other embodiments, the elongate member 202 can be constructed from a medical grade plastic using a molding process. In some embodiments, for example, the delivery head 210 can be constructed separately and/or using a different process from the elongate member 202. In such embodiments, the delivery head 210 can be coupled to the elongate member 202 using fasteners (e.g., screws, rivets or the like), an adhesive bond, a weld or the like. In other embodiments, the delivery head 210 and the elongate member 202 can be monolithically formed. Similarly, in some embodiments, the tip 246 of the carrier 240 can be constructed separately from the carrier 240 and can be coupled to the distal end portion 244 of the carrier 240 by an adhesive, a weld or the like.

The components of the implant 270 can be constructed from any suitable biocompatible material. In some embodiments, for example, the implant 270 can constructed from synthetic materials, such as, for example, nylon, silicone, polyethylene, polyester, polyimide, polyurethane, polypropylene, fluoropolymers or the like. In other embodiments, the implant 270 can constructed from natural materials, such as, for example materials derived from human and/or animal tissue. In yet other embodiments, the implant 270 can be constructed from a combination of synthetic and natural materials.

Although the implant 270 has been shown and described above without being associated with any specific anatomical structures, in some embodiments, the implant 270 can be associated with the repair of various pelvic dysfunctions. For example, in some embodiments, the implant can 270 can be an implant configured to be delivered into a pelvic region to repair a prolapsed uterus. Similarly, the implant 270 can be placed within the tissue T by any suitable method, For example, in some embodiments, portions of the implant 270 can be placed into the body through an obturator (e.g., using a transobturator approach). Moreover, the implants can be placed within the body using any suitable surgical approach (e.g., a retro-pubic, supra pubic, or pre-pubic approach).

Figure 11:
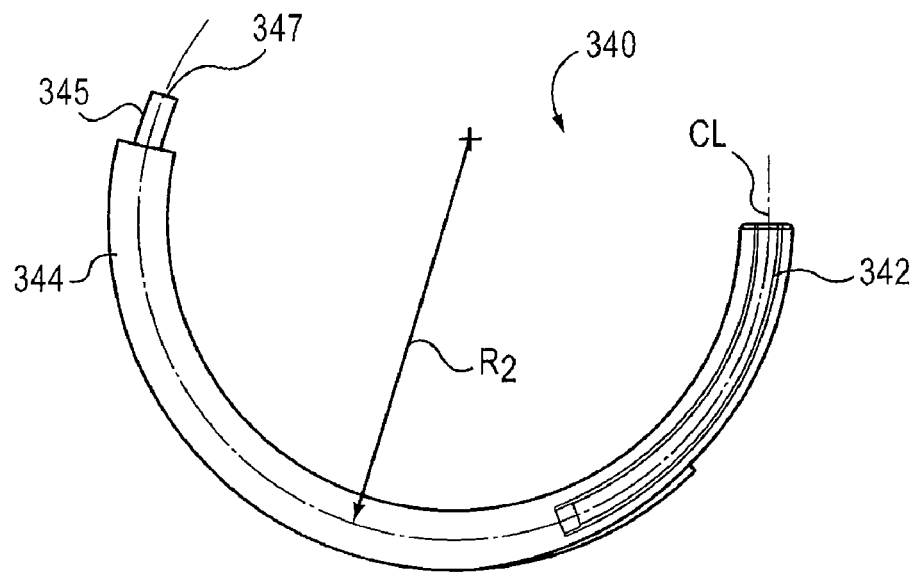
FIG. 11 is a side view of a carrier according to an embodiment of the invention.

Although the carrier 240 is shown and described as including a protrusion 245 having a tip 246 configured to pierce bodily tissue, in other embodiments, a carrier can be devoid of a protrusion and/or a tissue piercing tip. For example, in FIG. 11 shows a carrier 340 according to an embodiment of the invention that can be disposed within any suitable suturing device of the type shown and described herein. The carrier 340 has a proximal end portion 342 and a distal end portion 344, and defines a center line CL. The carrier 340 is curved such that the center line CL defines a radius of curvature $R_2$. As previously described, the proximal end portion 342 of the carrier 340 can be operatively coupled to an actuator (not shown in FIG. 11) such that the carrier 340 can be moved within an elongated member (not shown in FIG. 11), in a similar manner as that described above.

The distal end portion 344 of the carrier 340 includes a protrusion 345 having an engagement surface 347 disposed at the distal end thereof. The protrusion 345 differs from the protrusion 245 shown and described above, in that the protrusion 345 has a blunt end (i.e., the engagement surface 347) and is not configured to pierce bodily tissue. The engagement surface 347 is substantially normal to the center line CL of the carrier 340. Said another way, the center line CL of the carrier 340 and a line defined to include a portion of the engagement surface 347 intersect at an angle of approximately 90 degrees. For example, when the engagement surface 347 is planar, a plane defined by the engagement surface 347 intersects the center line CL of the carrier 340 at an angle of approximately 90 degrees.

Figure 12:
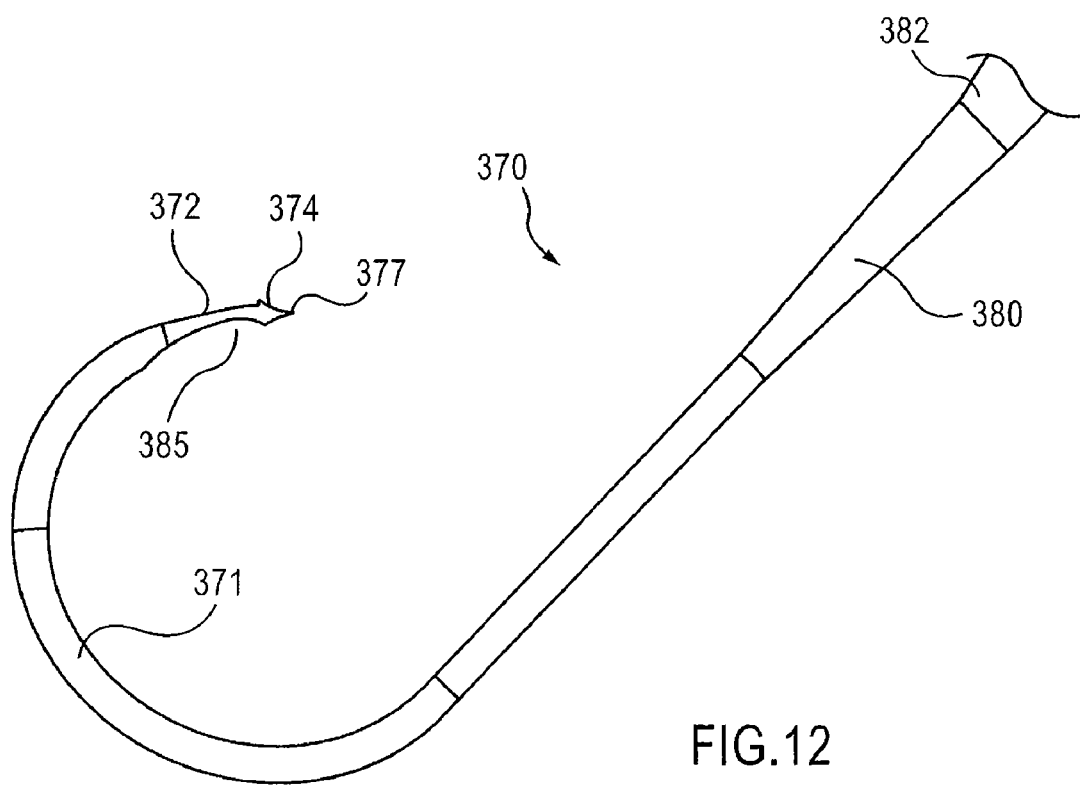
FIG. 12 is a side view of an implant according to an embodiment of the invention.
Figure 13:
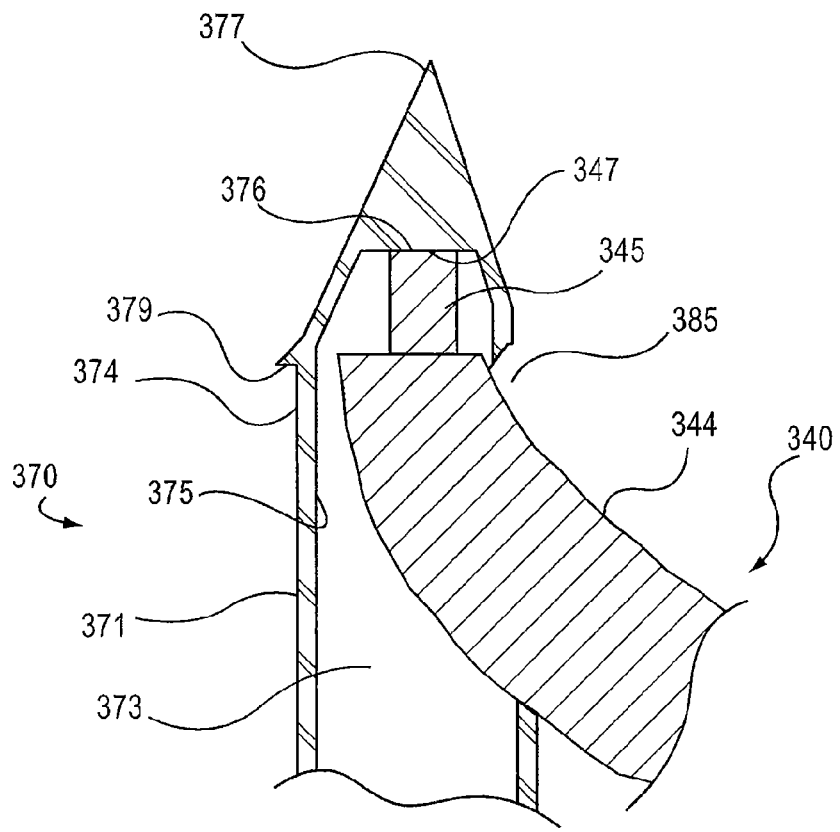
FIG. 13 is a cross-sectional view of the carrier shown in FIG. 11 disposed within the implant shown in FIG. 12.

FIGS. 12 and 13 show an implant 370 according to an embodiment of the invention that can be placed within the body using a suturing device including the carrier 340. The implant 370 includes a distal portion 371, a dilator 380, a sleeve 382 and a strap 384. The distal portion 371 of the implant 370 includes a connecting portion 372. The connecting portion 372 includes an outer surface 374, an inner surface 375 and an opening 385. The outer surface 374 defines a tip 377 configured to pierce bodily tissue. The outer surface 374 also defines a shoulder surface 379. The inner surface 375 includes a retention surface 376 and defines a lumen 373. The lumen 373 terminates at the retention surface 376. Said another way, the lumen 373 is a "blind hole" (i.e., the tip 377 does not define a passageway into the lumen 373). The dilator 380, sleeve 382 and strap 384 are similar to those described above with reference to FIG. 6, and are therefore not discussed in detail.

As shown in FIG. 13, the distal end portion 344 of the carrier 340 can be disposed within the opening 385 such that the protrusion 345 is received within the lumen 373 defined by the inner surface 375 of the connecting portion 372. Moreover, the protrusion 345 can be received within the lumen 373 such that the engagement surface 347 of the carrier 340 contacts and/or engages a portion of the retention surface 376 of the connector 372. In this manner, the engagement surface 347 of the carrier 340 can selectively limit movement of the connector 372 of the implant 370 relative to the carrier 340. Said another way, when the carrier 340 moves distally, the engagement surface 347 of the carrier 340 contacts and/or engages the retention surface 376 of the connecting portion 372 such that the implant 370 moves with the carrier 340 when the carrier 340 moves distally. When the carrier 340 moves proximally, however, the engagement surface 347 of the carrier 340 becomes disengaged from the retention surface 376 of the connecting portion 372 such that the carrier 340 can move proximally relative to the implant 370.

In some embodiments, when the carrier 340 moves distally the connecting portion 372 of the implant can be disposed within a retainer (not shown in FIGS. 11-13) similar to the retainer 230 shown and described above. Accordingly, when the carrier 340 moves proximally, the shoulder surface 379 can engage a portion of the retainer to maintain the position of the connecting portion 372 within the retainer.

Figure 14:
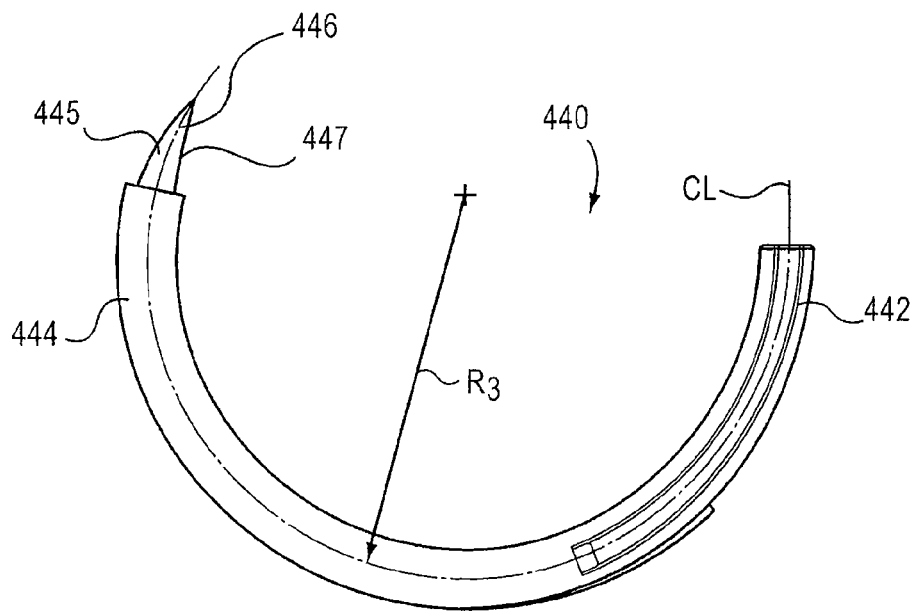
FIG. 14 is a side view of a carrier according to an embodiment of the invention.
Figure 15:
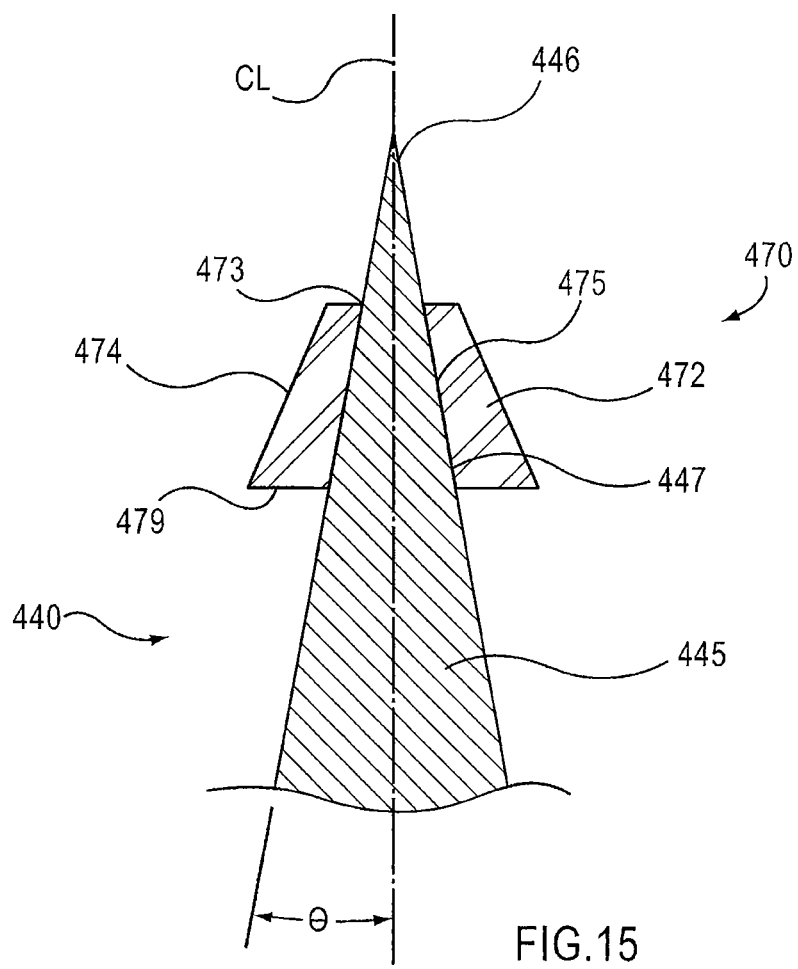
FIG. 15 is a cross-sectional view of the carrier shown in FIG. 14 disposed within an implant according to an embodiment of the invention.

Although the engagement surfaces of the carriers shown and described are planar surfaces substantially normal to the center line of the carrier, in other embodiments, an engagement surface can be angularly offset from the center line by an angle other than 90 degrees. Moreover, in other embodiments, an engagement surface can be a non-planar (i.e., curved) surface. For example, FIGS. 14 and 15 show a carrier 440 and according to an embodiment of the invention that can be disposed within any suitable suturing device of the type shown and described herein. The carrier 440 has a proximal end portion 442 and a distal end portion 444, and defines a center line CL. The carrier 440 is curved such that the center line CL defines a radius of curvature $R_3$. As previously described, the proximal end portion 442 of the carrier 440 can be operatively coupled to an actuator (not shown in FIGS. 14 and 15) such that the carrier 440 can be moved within an elongated member (not shown in FIGS. 14 and 15), as described above.

The distal end portion 444 of the carrier 440 includes a protrusion 445 having a tapered engagement surface 447. The protrusion 445 also defines a tip 446 configured to pierce bodily tissue, as described above. As shown in FIG. 15, the engagement surface 447 is angularly offset from the center line CL of the carrier 440 by an acute angle $\Theta$ (e.g., the taper angle). Moreover, because the engagement surface 447 includes the conical portion of the protrusion 445, the engagement surface 447 has a curved shape.

FIG. 15 shows a connector 472 of an implant 470 disposed about the protrusion 445 of the carrier 440. The connector 472 includes an outer surface 474 and an inner surface 475. The outer surface 474 defines a shoulder surface 479. The inner surface 475 defines a lumen 473 that extends through the connector 472. As shown, the protrusion 445 of the carrier 440 can be disposed within the lumen 473 such that that the engagement surface 447 contacts and/or engages a portion of the inner surface 475 of the connector 472. The lumen 473 can be sized such that the tip 446 is disposed outside of the lumen 473. In this manner, when the carrier 440 moves, tip 446 can pierce the targeted bodily tissue to define a passageway therethrough. Moreover, the engagement surface 447 of the carrier 440 can selectively limit movement of the connector 472 relative to the carrier 440. Said another way, when the carrier 440 moves distally, the engagement surface 447 of the carrier 440 contacts and/or engages the inner surface 475 of the connector 472 such that the implant (not shown in FIGS. 14 and 15) moves distally with the carrier 440.

When the carrier 440 moves proximally, however, the engagement surface 447 of the carrier 440 becomes disengaged from the inner surface 475 of the connector 472 such that the carrier 440 can move proximally relative to the inner surface 475 of the implant. For example, in some embodiments, the connector 472 of the implant 470 can be disposed within a retainer (not shown in FIGS. 11-13) similar to the retainer 230 shown and described above. Accordingly, when the carrier 440 moves proximally, the shoulder surface 479 of the connector 472 can engage a portion of the retainer to maintain the position of the connecting portion 472 within the retainer.

Although the engagement surface 447 is shown in FIG. 15 as being angularly offset from the center line CL of the carrier 440 by a non-zero angle Θ, in some embodiments, the engagement surface 447 of the carrier 440 can be substantially parallel to the center line CL of the carrier 440. Said another way, in some embodiments, the engagement surface 447 of the carrier 440 can be coaxial with the center line CL of the carrier 440. In some such embodiments, for example, the engagement surface of the carrier can be configured to form an interference fit with the inner surface of the connector to selectively limit distal and/or proximal movement of the connector relative to the carrier and/or retain the connector to the carrier.

Figure 16:
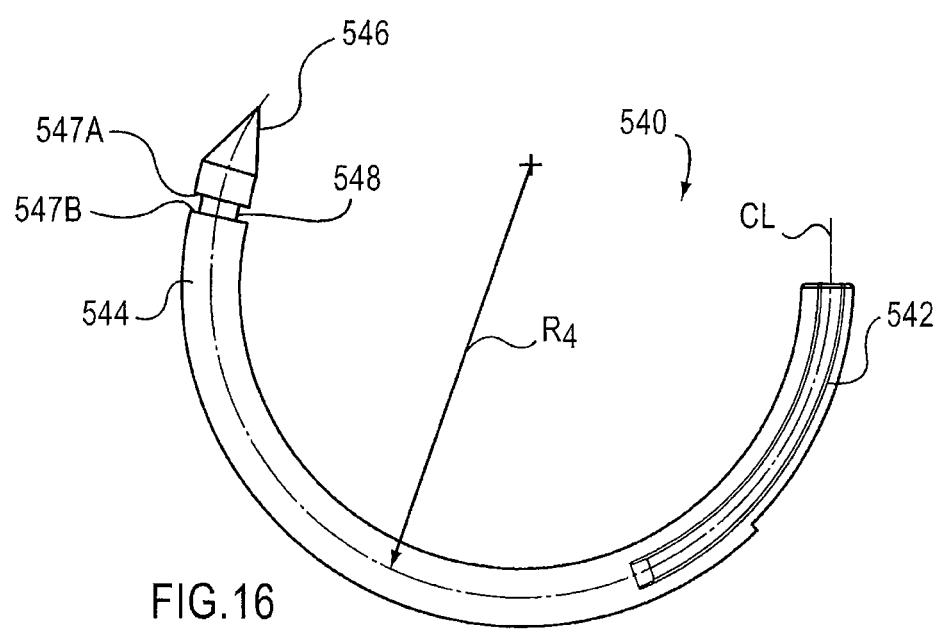
FIG. 16 is a side view of a carrier according to an embodiment of the invention.
Figure 18:
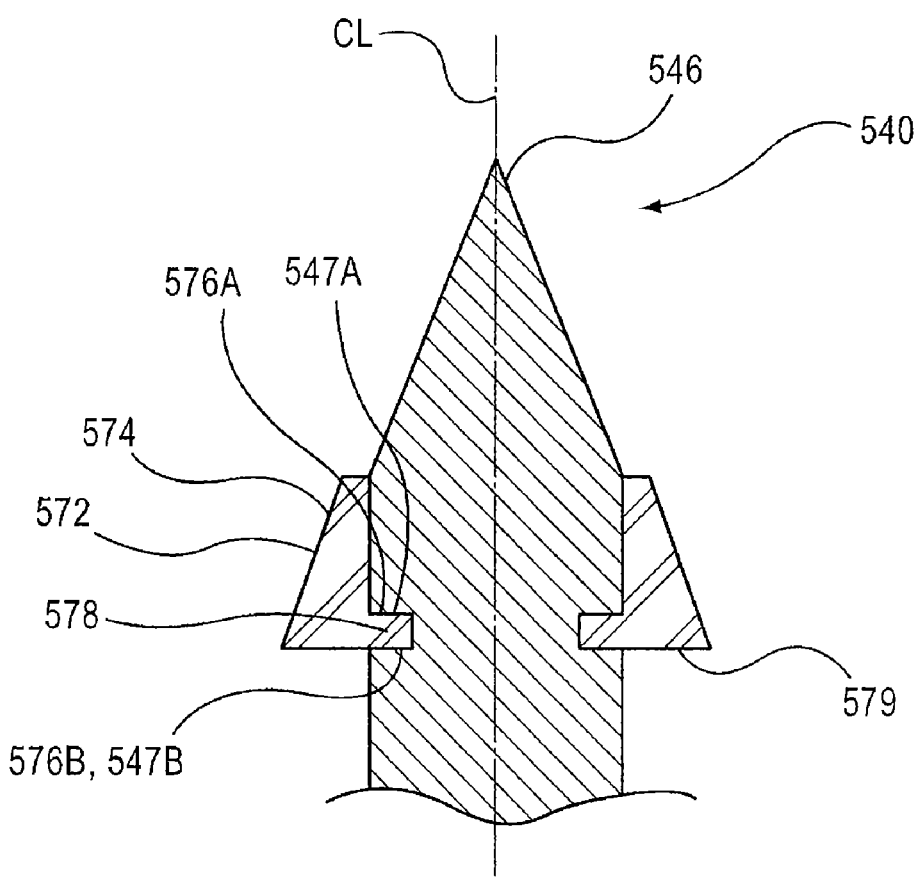
FIG. 18 is a cross-sectional view of the carrier shown in FIG. 16 disposed within the portion of the implant shown in FIG. 17.

Although the carriers are shown and described above as including a single, continuous retention surface, in other embodiments, a carrier can include multiple surfaces. For example, FIGS. 16 and 18 show a carrier 540 and according to an embodiment of the invention that can be disposed within any suitable suturing device of the type shown and described herein. The carrier 540 has a proximal end portion 542 and a distal end portion 544, and defines a center line CL. The carrier 540 is curved such that the center line CL defines a radius of curvature $R_4$. As previously described, the proximal end portion 542 of the carrier 540 can be operatively coupled to an actuator (not shown in FIGS. 16 and 18) such that the carrier 540 can be moved within an elongated member (not shown in FIGS. 16 and 18), as described above.

The distal end portion 544 of the carrier 540 includes a first engagement surface 547A and a second engagement surface 547B opposite the first engagement surface 547A. The first engagement surface 547A and the second engagement surface 547B collectively define an annular opening or groove 548. The distal end portion 544 of the carrier 540 also includes a tip 546 configured to pierce bodily tissue, as described above.

Figure 17:
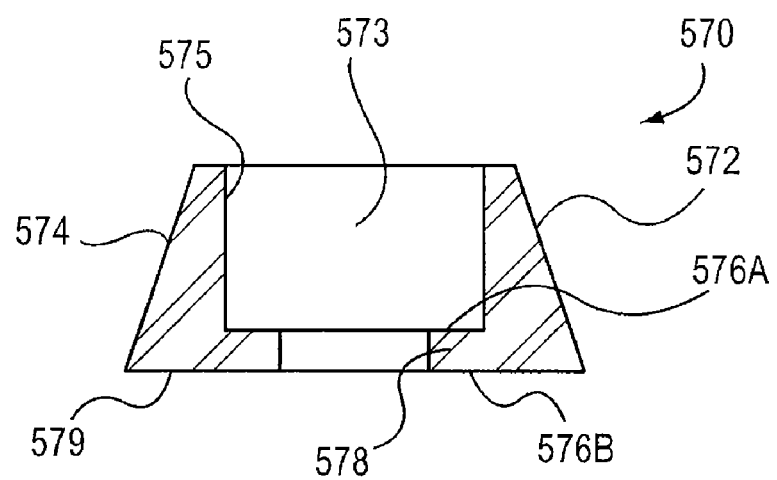
FIG. 17 is a cross-sectional view of a portion of an implant according to an embodiment of the invention.

FIG. 17 shows a connector 572 of an implant 570 configured to be disposed about the distal end portion 544 of the carrier 540. The connector 572 includes an outer surface 574 and an inner surface 575. The inner surface 575 defines a lumen 573 that extends through the connector 572. The inner surface 575 includes a first retention surface 576A and a second retention surface 576B opposite the first retention surface 576A. The first retention surface 576A and the second retention surface 576B collectively define an annular protrusion 578. The proximal end of the connector 572 includes a shoulder surface 579 configured to engage a retainer (not shown in FIGS. 16-18), as described below.

As shown in FIG. 18, the distal end portion 544 of the carrier 540 can be disposed within the lumen 573 such that that the protrusion 578 of the connector 572 is received within the groove 548 of the carrier 540. In some embodiments, the protrusion 578 and the groove 548 can be sized such that they collectively form an interference or "snap" fit between the carrier 540 and the connector 572. Said another way, in some embodiments, the protrusion 578 of the connector 572 matingly engages the groove 548 of the carrier 540 to removably couple the connector 572 to the carrier 540.

When the protrusion 578 of the connector 572 is received within the groove 548 of the carrier 540, the first engagement surface 547A contacts and/or engages the first retention surface 576A and the second engagement surface 547B contacts and/or engages the second retention surface 576B. In this manner, the connector 572 can be retained in position about the carrier 540. Accordingly, when the carrier 540 moves, the first engagement surface 547A of the carrier 540 can selectively limit the proximal movement of the connector 572 relative to the carrier 540. Similarly, when the carrier 540 moves, the second engagement surface 547B of the carrier 540 can selectively limit the distal movement of the connector 572 relative to the carrier 540. When the connector is retained within the delivery head of the suturing device (not shown in FIGS. 16-18) as described above, the protrusion 578 and the groove 548 can be sized such that the force imparted by the retainer (not shown in FIG. 16-18) on the shoulder surface 579 is sufficient to move the protrusion 578 from the groove 548, thereby releasing the connector 572 from the distal end portion 544 of the carrier 540.

Figure 19:
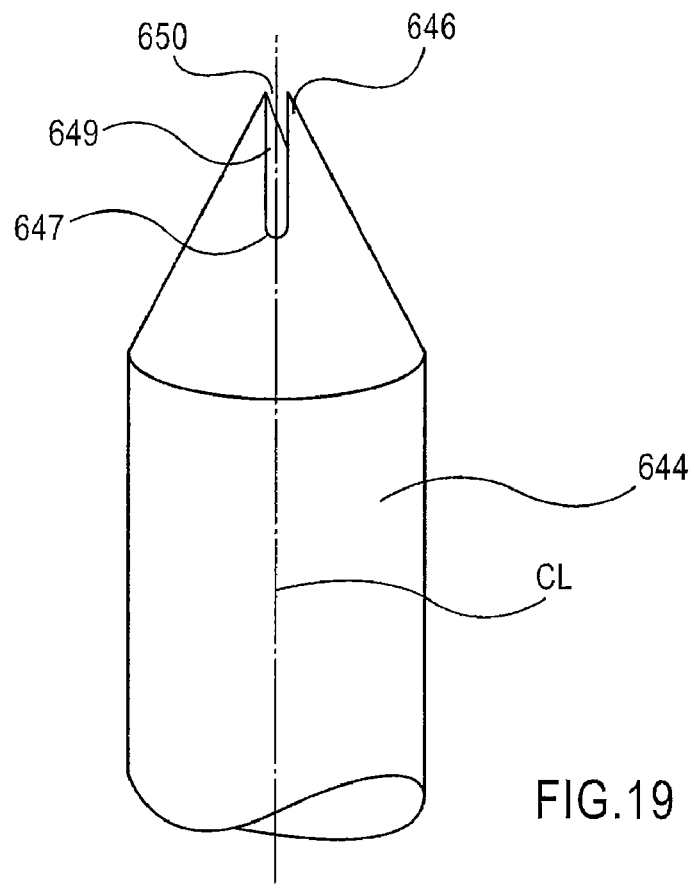
FIG. 19 is a perspective view of a distal end portion of a carrier according to an embodiment of the invention.

FIG. 19 shows a distal end portion 644 of a carrier and according to an embodiment of the invention that can be disposed within any suitable suturing device of the type shown and described herein. As described above, the carrier defines a center line CL. In some embodiments, the carrier can be curved such that the center line CL defines a radius of curvature, as described above. The distal end portion 644 of the carrier includes a tip 646 and defines a retention slot 649. The tip 646 is configured to pierce bodily tissue, as described above. The slot 649 includes an opening 650 at the distal end of the tip 646 and is bounded by a surface 647 disposed proximally from the distal end of the tip 646. The slot 649 is substantially parallel to and coaxial with the center line CL.

Figure 20:
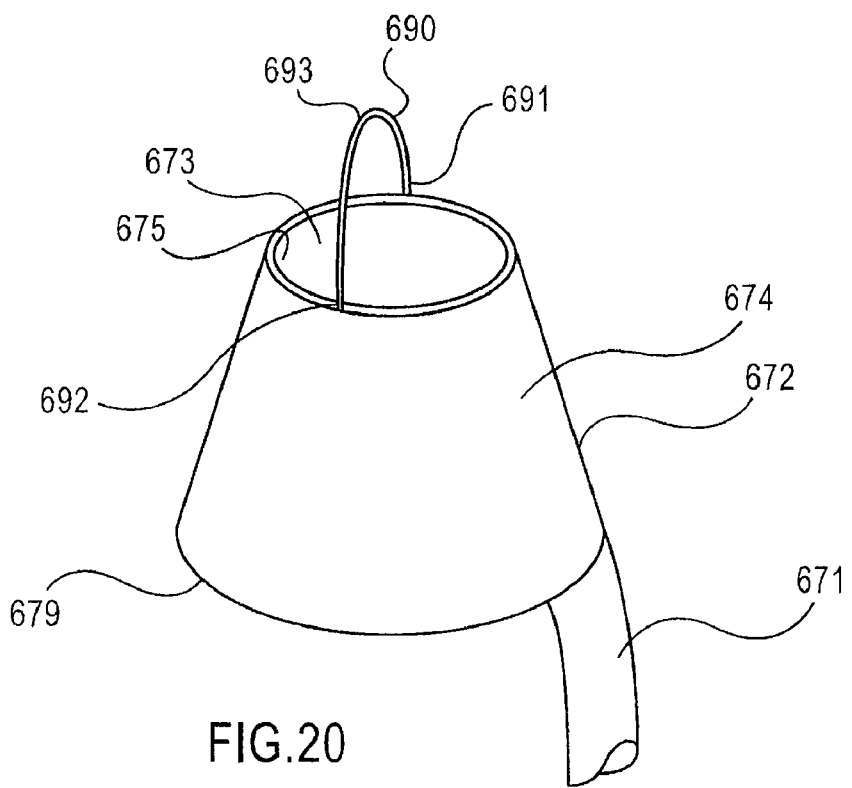
FIG. 20 is a perspective view of a portion of an implant according to an embodiment of the invention.

FIG. 20 shows a distal end portion 671 of an implant configured to be disposed about the distal end portion 644 of the carrier according to an embodiment of the invention. The distal end portion 671 of the implant includes a connector 672. The connector 672 includes a tapered outer surface 674, an inner surface 675 and a retention member 690. As described above, the inner surface 675 defines a lumen 673 that extends through the connector 672. The outer surface 674 includes a shoulder surface 679 configured to engage a retainer (not shown in FIGS. 16-18).

The retention member 690 includes a first end portion 691, a second end portion 692 and a central portion 693. The first end portion 691 and the second end portion 692 are each coupled to the outer surface 674 of the connector 672 such that the retention member 690 forms a loop at the distal end of the connector 672. The retention member 690 can be coupled to the outer surface 674 in any suitable fashion. In some embodiments, for example, the retention member 690 can be coupled to the outer surface 674 by an adhesive, by a thermal bond, by a weld or the like. In other embodiments, the connector 672 and the retention member 690 can be monolithically formed. Similarly, the retention member 690 can be constructed from any suitable material, such as, for example, a flexible polymer, a rigid polymer, a metallic alloy or the like.

Figure 21:
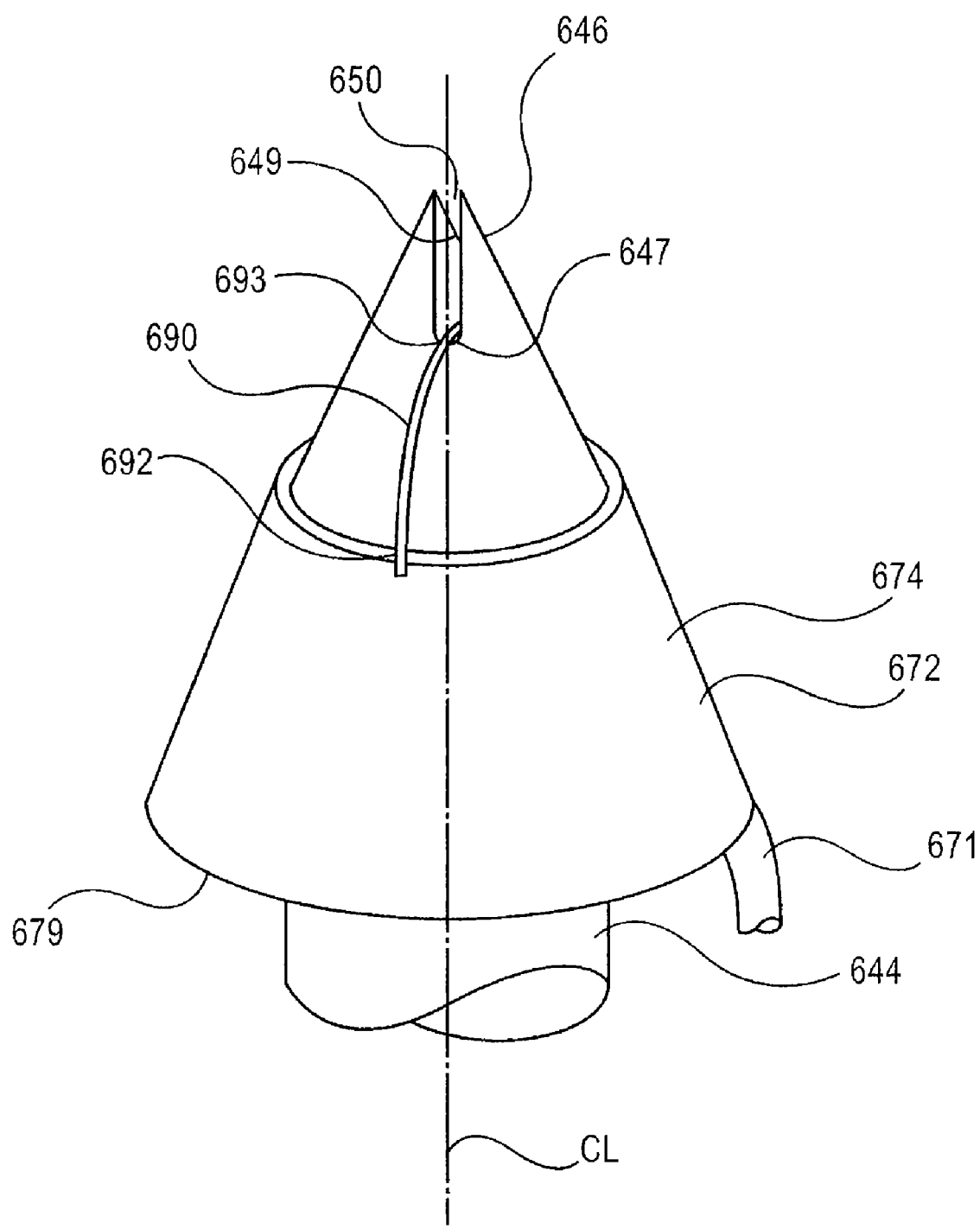
FIG. 21 is a perspective view of the distal end portion of the carrier shown in FIG. 19 disposed within the portion of the implant shown in FIG. 20.

As shown in FIG. 21, the distal end portion 644 of the carrier can be disposed within the lumen 673 such that that the retention member 690 of the connector 672 is disposed through the opening 650 and is received within the slot 649. In this manner, the central portion 693 of the retention member 690 can contact and/or engage the surface 647 to selectively maintain a position of the connector 672 relative to the distal end portion 644 of the carrier. Said another way, when the carrier moves distally, the surface 647 of the carrier contacts and/or engages the central portion 693 of the retention member 690 such that the distal portion 671 of the implant moves distally with the carrier.

When the carrier moves proximally, however, the carrier can move relative to the retention member 690 of the implant. Accordingly, the retention member 690 can move outside of the slot 649 through the opening 650. For example, in some embodiments, the connector 672 can be disposed within a retainer (not shown in FIG. 21) similar to the retainer 230 shown and described above. Accordingly, when the carrier moves proximally, the shoulder surface 679 of the connector 672 can engage a portion of the retainer to maintain the position of the connecting portion 672 within the retainer. The proximal movement of the carrier thereby causes the connector 672 to become disposed apart from the distal end portion 644 of the carrier.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above. Thus, the breadth and scope of the invention should not be limited by any of the above-described embodiments. While the invention has been particularly shown and described with reference to specific embodiments thereof, it will be understood that various changes in form and details may be made.

For example, although the carrier 240 is shown and described above as being configured to move along a circular path as shown in FIGS. 7-10, in some embodiments a carrier can be configured to move along a path having any suitable shape. For example, in some embodiments, a carrier can be configured to move along a path having a non-circular curved shape (e.g., a path having multiple radii of curvature) In some embodiments, a carrier can be configured to move along a path having a shape that is curved in three dimensions (e.g., a "corkscrew" shaped path).

Although the carrier 240 is shown and described as having a circular cross-sectional area, in other embodiments, the carrier can have any suitable cross-sectional shape. For example, in some embodiments, a carrier can have an oval shape. In other embodiments, a carrier can have a rectangular shape.

Although the carrier 240 is shown and described herein as including a tip 246 configured to pierce tissue, in some embodiments, a carrier can be configured to include multiple tips that can be interchangeably coupled to the distal end portion of the carrier. In this manner, for example, a user can select a tip having a desired size and/or shape. For example, in some embodiments, a carrier can include a first tip configured to pierce bodily tissue of a first type (e.g., tissue composed primarily of tendons) and a second tip configured to pierce bodily tissue of a second type (e.g., tissue composed primarily of muscle).

Although the retainers shown and described above define multiple openings, in some embodiments, a retainer can define a single opening. Similarly, in some embodiments, a retainer can define an opening having any suitable shape and/or size such that the retainer can retain a portion of an implant, as described herein.

Although the retainers shown and described above include ribs that define multiple openings and deflect to allow a connector of an implant to pass therethrough, in some embodiments, a retainer can include ribs that are substantially rigid. In such embodiments, for example, the connector of the implant can be configured to deflect to all the connector to pass through the openings defined by the ribs such that the connector can be retained within the retainer.

Although the connectors and/or connecting portions of the implants are shown and described as including a shoulder surface configured to "catch" or be retained within a retainer, in some embodiments, an implant can include a connecting portion configured to be retained within the bodily tissue. For example, in some embodiments, an implant can include a connecting portion having roughened and/or jagged edges to anchor the implant within the tissue T. In some embodiments, for example, a connecting portion can include protrusions or "tangs" along its outer edge to enhance the anchoring of the connecting portion within the bodily tissue.

Although various embodiments have been described as having particular features and/or combinations of components, other embodiments are possible having a combination of any features and/or components from any of embodiments as discussed above. For example, one such embodiment includes a carrier being devoid of a tissue-piercing tip (see e.g., carrier 340) and a having a outer surface that defines an annular groove configured to form an interference fit with a connecting portion of an implant (see e.g., carrier 540).

What is claimed is:

1. An apparatus, comprising:
   a carrier configured to be movably disposed within a channel defined by an elongate member, the carrier including:
   a proximal end portion configured to be coupled to an actuator; and
   a distal end portion including a protrusion and an engagement surface, the protrusion having a tip configured to pierce bodily tissue, the protrusion configured to be received within a lumen defined by a connecting portion of an implant such that the tip extends through the lumen defined by the connecting portion of the implant, the engagement surface configured to engage a portion of the connecting portion of the implant to limit movement of the connecting portion of the implant relative to the protrusion, the engagement surface moving from a location within the channel when the carrier is in a first position to a location within a receiver defined by the elongate member when the carrier is moved to a second position.

2. The apparatus of claim 1, wherein the engagement surface is configured to limit movement of the connecting portion of the implant proximally relative to the protrusion and allow movement of the connecting portion of the implant distally relative to the protrusion.

3. The apparatus of claim 1, wherein a center line of the distal end portion of the carrier defines a radius of curvature.

4. The apparatus of claim 1, wherein the at least the distal end portion of the carrier is arcuate.

5. The apparatus of claim 1, wherein the distal end portion of the carrier is devoid of an opening.

6. The apparatus of claim 1, wherein a diameter of the protrusion is smaller than a diameter of the distal end portion of the carrier.

7. The apparatus of claim 1, wherein a diameter of the protrusion is approximately one half of a diameter of the distal end portion of the carrier.

8. The apparatus of claim 1, wherein the engagement surface is further configured to engage a portion of the connecting portion of the implant to retain the protrusion within the lumen defined by the connecting portion of the implant.

9. The apparatus of claim 1, wherein the engagement surface is substantially normal to a center line of the distal end portion of the carrier.

10. The apparatus of claim 1, wherein the engagement surface is configured to form an interference fit with the portion of the connecting portion of the implant.

11. The apparatus of claim 1, wherein the engagement surface is configured to matingly engage with a corresponding surface of the portion of the connecting portion of the implant.

12. The apparatus of claim 1, wherein the connecting portion of the implant includes at least one of a suture, a tapered connecting ring, a dilator, an implant strap, an implant sleeve or a soft tissue anchor.

13. An apparatus, comprising:
an elongate member having a proximal end portion and a distal end portion, the elongate member defining an opening and a retainer;
an actuator coupled to the proximal end portion of the elongate member; and
a carrier movably coupled to the distal end portion of the elongate member, the carrier including a proximal end portion and a distal end portion, the proximal end portion configured to be coupled to the actuator, the distal end portion configured to be received within a lumen defined by a connecting portion of an implant, the distal end portion including an engagement surface configured to engage the connecting portion of the implant to limit movement of the connecting portion of the implant relative to the distal end portion of the carrier, the distal end portion of the carrier being configured to extend from the opening defined by the elongate member to the retainer defined by the elongate member.

14. The apparatus of claim 13, wherein the engagement surface is configured to limit movement of the connecting portion of the implant proximally relative to the distal end portion of the carrier and allow movement of the connecting portion of the implant distally relative to the distal end portion of the carrier.

15. The apparatus of claim 13, wherein the distal end portion of the carrier includes a protrusion having a tip configured to pierce bodily tissue, the protrusion being configured to be received within the lumen defined by the connecting portion such that the tip extends through the lumen to an area outside of the connecting portion.

16. The apparatus of claim 13, wherein a portion of the distal end portion of the carrier is configured to form an interference fit with the connecting portion of the implant.

17. The apparatus of claim 13, wherein:
the distal end portion of the elongate member defines a channel; and
the carrier is disposed within the channel.

18. The apparatus of claim 13, wherein the elongate member is configured to be coupled to the connecting portion of the implant when the distal end portion of the carrier is disposed within the lumen defined by the elongate member.

19. An apparatus, comprising:
an elongate member having a distal end portion, the elongate member defining an opening and a retainer; and
a carrier movably coupled to the elongate member for movement between a first position and a second position, when the carrier is in the second position, a distal end portion of the carrier extends from the opening defined by the elongate member to the retainer,
the distal end portion of the carrier configured to be received within a lumen defined by a connecting portion of an implant, the distal end portion including an engagement surface configured to engage the connecting portion of the implant to retain the distal end portion of the carrier within the lumen defined by the connecting portion of the implant when the carrier is moved between the first position and the second position.

20. The apparatus of claim 19, wherein:
the distal end portion of the elongate member defines a channel,
the distal end portion of the carrier being disposed entirely within the channel when the carrier is in the first position,
the distal end portion of the carrier being disposed outside of the channel when the carrier is in the second position.

21. The apparatus of claim 19, wherein the distal end portion of the carrier includes a protrusion having a tip configured to pierce bodily tissue, the protrusion being configured to be received within the lumen defined by the connecting portion such that the tip extends through the lumen to an area outside of the connecting portion of the implant.

22. The apparatus of claim 19, wherein the engagement surface is configured to matingly engage with a corresponding surface of the connecting portion of the implant.

23. The apparatus of claim 19, wherein the retainer configured to receive a portion of the distal end portion of the carrier when the carrier is in the second position.

24. The apparatus of claim 19, wherein
the engagement surface is configured to retain the distal end portion of the carrier within the lumen defined by the connecting portion of the implant such that the connecting portion of the implant is moved distally when the carrier is moved between the first position and the second position, and
the retainer defining an opening configured to receive and retain the connecting portion of the implant when the carrier is in the second position.

* * * * *